(12) United States Patent
Liu et al.

(10) Patent No.: US 11,771,387 B2
(45) Date of Patent: Oct. 3, 2023

(54) FAST 3D RADIOGRAPHY USING MULTIPLE PULSED X-RAY SOURCES IN MOTION

(71) Applicants: Jianqiang Liu, Campbell, CA (US); Linbo Yang, Pleasanton, CA (US); Manat Maolinbay, Gilroy, CA (US); Xiaohui Tang, SuZhou (CN); Chwen-yuan Ku, San Jose, CA (US); Yichin Liu, Campbell, CA (US)

(72) Inventors: Jianqiang Liu, Campbell, CA (US); Linbo Yang, Pleasanton, CA (US); Manat Maolinbay, Gilroy, CA (US); Xiaohui Tang, SuZhou (CN); Chwen-yuan Ku, San Jose, CA (US); Yichin Liu, Campbell, CA (US)

(73) Assignee: AIXSCAN Inc., Sunnyvale, CA (US)

( * ) Notice: Subject to any disclaimer, the term of this patent is extended or adjusted under 35 U.S.C. 154(b) by 153 days.

(21) Appl. No.: 17/149,133

(22) Filed: Jan. 14, 2021

(65) Prior Publication Data

US 2021/0228168 A1 Jul. 29, 2021

Related U.S. Application Data

(60) Provisional application No. 62/967,325, filed on Jan. 29, 2020.

(51) Int. Cl.
*A61B 6/00* (2006.01)
*A61B 6/02* (2006.01)

(52) U.S. Cl.
CPC .......... *A61B 6/4476* (2013.01); *A61B 6/4007* (2013.01); *A61B 6/486* (2013.01); *A61B 6/502* (2013.01); *A61B 6/542* (2013.01); *A61B 6/025* (2013.01); *A61B 6/027* (2013.01); *A61B 6/482* (2013.01)

(58) Field of Classification Search
CPC ....... A61B 6/027; A61B 6/025; A61B 6/4476; A61B 6/482; A61B 6/4007; A61B 6/486
See application file for complete search history.

(56) References Cited

U.S. PATENT DOCUMENTS 7,751,528 B2 * 7/2010 Zhou ..................... G06T 11/006
378/21
8,724,872 B1 * 5/2014 Ziskin .................. A61B 6/5205
382/131

(Continued)

*Primary Examiner* — Dani Fox
*Assistant Examiner* — Soorena Kefayati
(74) *Attorney, Agent, or Firm* — Patent PC; Bao Tran (57) ABSTRACT

An X-ray imaging system using multiple pulsed X-ray sources in motion to perform high efficient and ultrafast 3D radiography is presented. There are multiple pulsed X-ray sources mounted on a structure in motion to form an array of sources. The multiple X-ray sources move simultaneously relative to an object on a pre-defined arc track at a constant speed as a group. Each individual X-ray source can also move rapidly around its static position in a small distance. When an X-ray source has a speed that is equal to group speed but with opposite moving direction, the X-ray source and X-ray flat panel detector are activated through an external exposure control unit so that source stay momentarily standstill. It results in much reduced source travel distance for each X-ray source. 3D scan can cover much wider sweep angle in much shorter time and image analysis can also be done in real-time.

15 Claims, 9 Drawing Sheets

(56) References Cited

U.S. PATENT DOCUMENTS

| | | | | |
|---|---|---|---|---|
| 2005/0226371 A1* | 10/2005 | Kautzer | ............... | A61B 6/502 378/37 |
| 2008/0002809 A1* | 1/2008 | Bodduluri | ............ | A61B 6/4007 378/41 |
| 2009/0033940 A1* | 2/2009 | Sanpitak | ............... | A61B 6/547 356/432 |
| 2009/0323893 A1* | 12/2009 | Hanke | ................. | A61B 6/4007 382/131 |
| 2010/0091940 A1* | 4/2010 | Ludwig | ............... | A61B 6/4028 378/22 |
| 2010/0246759 A1* | 9/2010 | Ogura | .................. | A61B 6/469 378/62 |
| 2011/0002441 A1* | 1/2011 | Vogtmeier | .......... | A61B 6/4007 378/21 |
| 2011/0080992 A1* | 4/2011 | Dafni | .................. | A61B 6/4014 378/9 |
| 2012/0008739 A1* | 1/2012 | Hoernig | ............. | A61B 6/025 378/37 |
| 2012/0195403 A1* | 8/2012 | Vedantham | .......... | A61B 6/022 378/62 |
| 2013/0294568 A1* | 11/2013 | Lee | ....................... | A61B 6/025 378/4 |
| 2014/0209806 A1* | 7/2014 | Nishino | .............. | A61B 6/4007 250/363.01 |
| 2015/0131775 A1* | 5/2015 | Yorkston | ............. | A61B 6/4405 378/17 |
| 2016/0249869 A1* | 9/2016 | Papalazarou | ....... | A61B 6/4266 378/62 |
| 2016/0256128 A1* | 9/2016 | Wang | .................... | A61B 6/025 |
| 2016/0262710 A1* | 9/2016 | Baek | ..................... | A61B 6/4435 |
| 2017/0311911 A1* | 11/2017 | Kim | ...................... | A61B 6/032 |
| 2018/0289348 A1* | 10/2018 | Cox | ..................... | A61B 6/4078 |
| 2019/0209107 A1* | 7/2019 | Vogtmeier | ............. | A61B 6/54 |
| 2019/0388050 A1* | 12/2019 | Lee | ........................ | A61B 6/54 |
| 2020/0000423 A1* | 1/2020 | Mohammadi | .......... | H01J 35/13 |
| 2020/0100745 A1* | 4/2020 | Sato | ....................... | A61B 6/488 |
| 2020/0100747 A1* | 4/2020 | Matsuura | .............. | A61B 6/107 |
| 2020/0100749 A1* | 4/2020 | Makino | ................. | A61B 6/027 |
| 2020/0315559 A1* | 10/2020 | Steinhauser | ......... | A61B 6/4291 |
| 2020/0321183 A1* | 10/2020 | Xing | .................... | H01J 35/045 |
| 2021/0106291 A1* | 4/2021 | Shin | ........................ | A61B 6/42 |

* cited by examiner

FAST 3D RADIOGRAPHY USING MULTIPLE PULSED X-RAY SOURCES IN MOTION

This application claims priority to Provisional Ser. 62/967,325, the content of which is incorporated by reference.

FIELD OF THE INVENTION

This patent specification is in the field of 3D X-ray radiography systems and methods and particularly to using pulsed X-ray source and large field, digital flat panel X-ray detectors.

BACKGROUND OF THE INVENTION

There is one kind of digital X-ray 3D radiography like mammography, also digital tomosynthesis (DTS), is a method for performing high-resolution limited-angle tomography at radiation dose levels comparable with conventional radiography.

These digital tomosynthesis systems typically use an X-ray source mounted at one end of a rotatable c-arm assembly and a digital flat panel detector at the other. Between the x-ray source and the detector is a device that can compress and immobilize a breast. Compression of the breast is necessary for the reasons of reduced X-ray scatter, reduced radiation dose, more uniform optical density across the detector and improved visualization of anatomy.

Tomosynthesis can be used to screen for early signs of breast cancer in women with no symptoms. This type of imaging can also be used as a diagnostic tool for women that are having breast cancer symptoms. Tomosynthesis is an advanced type of mammography. Digital Breast Tomosynthesis (DBT) detects more caners and has fewer false positive recalls and more precise lesion localization than that of 2D mammography.

When tomosynthesis is performed, the X-ray source would need to move in an arc around the breast. While the X-ray source moves around the breast, a series of low dose X-ray images are acquired at different angles.

The collected data set permits the reconstruction of parallel planes. Each plane is in focus, and those that are out-of-plane tissue images are blurred. Usually, a wider sweep angle would generate more data projections and result in better 3D resolution, but it takes a longer time. Data processing is a manufacturer-specific because different reconstruction algorithms might be used.

It should be emphasized that these kinds of digital tomosynthesis systems and methods can also be applied to other X-ray 3D radiography applications such as X-ray 3D chest diagnosis system for COVID, X-ray 3D Non-Destructive Test (NDT) system, and X-ray 3D security inspection system.

There are prior arts that are with the single X-ray source and single flat panel to perform X-ray 3D radiography. However, there are disadvantages among prior arts.

The main disadvantage is that it takes a very long time for a single X-ray source to acquire good data projections. It is true for both continuous mode and step-and-shoot mode. In continuous mode, the X-ray source emits X-ray while it is moving; in step-and-shoot mode, the X-ray source moves to a location, stops and emits X-ray, and continues moving to the next location.

Although all patients hope X-ray imaging could be done as fast as possible, there is a minimum X-ray source travel sweep angle requirement. If the sweep angle is too small so that the X-ray source can travel less and the total time needed is less, then the system will have smaller numbers of data projections. The smaller number of data projections would result in lower depth resolution and loss of details perception. If the sweep angle needs to be large enough for good data projections for better 3D resolution, then a single X-ray source may mechanically travel too long that patients will feel uncomfortable and cannot hold breast standstill anymore. In some cases, a 50-degree sweep would take as long as about half a minute.

The second disadvantage is that it is difficult to do real-time reconstruction because the whole thing is slow. Usually, prior art takes tens of seconds to finish sweeping.

SUMMARY OF INVENTION

In a first aspect, a system to provide fast 3D radiography using multiple pulsed X-ray sources in motion with a primary motor stage moving freely on an arc rail with a predetermined shape; a primary motor that engages with said primary motor stage and controls a speed of the primary motor stage; a plurality of secondary motor stages coupled to said primary motor stage and move along a direction of the arc rail; a plurality of secondary motors, each engaging a secondary motor stage and controlling a speed of secondary motor stage; a plurality of X-ray sources each moved by a secondary motor stage; a supporting frame structure that provides housing for the primary motor stage and secondary motor stages; and a flat panel detector to receive X-ray imaging data.

In a second aspect, a method of fast 3D radiography using multiple pulsed X-ray sources in motion includes positioning a primary motor stage and one or more secondary motor stages to a predetermined initial location; sweeping the primary motor stage at a predetermined constant speed by said primary motor; oscillating each of the secondary motor stages by a corresponding secondary motor with a predetermined sequence; electrically activating an X-ray source and a flat panel detector when a secondary motor stage moves in an opposite direction to that of the primary motor stage and at a selected speed of the primary motor stage; and acquiring image data from the X-ray source with a flat panel.

In another aspect, an X-ray imaging system using multiple pulsed X-ray sources in motion to perform ultrafast, high efficient 3D radiography is presented. In the system, there are multiple pulsed X-ray sources mounted on a structure in motion to form an array of the source. The multiple X-ray sources move simultaneously around an object on a pre-defined track at a constant speed of a group. Each individual X-ray source can also move rapidly around its static position of a small distance. When an individual X-ray source has a speed that equals to group speed but an opposite moving direction, the individual X-ray source is triggered through an external exposure control unit. This arrangement allows the X-ray source to stay relatively standstill during the X-ray pulse trigger exposure duration. Multiple X-ray sources result in a much-reduced source travel distance for individual X-ray sources. X-ray receptor is an X-ray flat panel detector. 3D radiography image projection data can be acquired with an overall much wider sweep in a much shorter time period, and image analysis can also be done in real-time while the scan goes.

In another aspect, an X-ray imaging system using multiple pulsed X-ray sources in motion to perform high efficient and ultrafast 3D radiography includes multiple pulsed X-ray sources mounted on a structure in motion to form an array of sources. The multiple X-ray sources move simultaneously relative to an object on a pre-defined arc track at a constant speed as a group. Each individual X-ray source can also move rapidly around its static position at a small distance. When an individual X-ray source has a speed that is equal to group speed, but with opposite moving direction, the individual X-ray source and X-ray detector are activated through an external exposure control unit. This arrangement allows the X-ray source to stay relatively standstill during the X-ray source activation and X-ray detector exposure. X-ray receptor is an X-ray flat panel detector. Multiple X-ray source in motion operation results in a much-reduced source travel distance for individual X-ray sources. 3D radiography image data can be acquired with an overall wider sweep angle in a much shorter time, and image analysis can also be done in real-time while the scan goes.

In implementations, the X-ray can also be randomly activated from one of any sources in the array using a random-firing scheme. Results of each and accumulated analysis determines the next X-ray source and exposure condition. 3D X-ray radiography images are reconstructed based on each image with an angled geometry of X-ray exposure source. Much broader applications include 3D mammography or Tomosynthesis, chest 3D radiography for COVID or fast 3D NDT, fast 3D X-ray security inspection.

Advantages of the above systems may include one or more of the following. The various embodiment of multiple X-ray sources in motion is used in a novel ultrafast 3D radiography system.

The first advantage is that system overall is several times faster. Each x-ray source would only need to mechanically travel a small fraction of the whole distance in an arc trajectory. It greatly reduces the amount of data acquisition time that is needed for a patient at the X-ray diagnosis machine. The second advantage is that image analysis can also be done in real-time as the scan goes. Judgment on the images taken will have an impact on the X-ray source position for the next shot. There is no need to wait until the finish of the whole image acquisition to do layered image reconstruction.

The third advantage is that acquisition of high resolution, and high contrast images are possible due to reduction of motion artifacts. Each X-ray source is also mounted on a substructure that vibrates the source around its origin. The composition of vibration speed and track speed leads to the relative standstill position of the X-ray sources at the moment the individual X-ray source is activated.

The fourth advantage is that system can go a much wider sweep to acquire more data projections while being faster. More data projections mean better image construction that would lead to a reduced misdiagnosis rate.

The fifth advantage is that because of a wider angle and faster imaging acquisition, and it is possible to add time components to 3D spatial imaging to form 4D imaging data set.

The present invention has been described in terms of the preferred embodiment, and it is recognized that equivalents, alternatives, and modifications, aside from those expressly stated, are possible and within the scope of the appending claims.

DETAILED DESCRIPTION OF PREFERRED EMBODIMENTS

Figure 1:
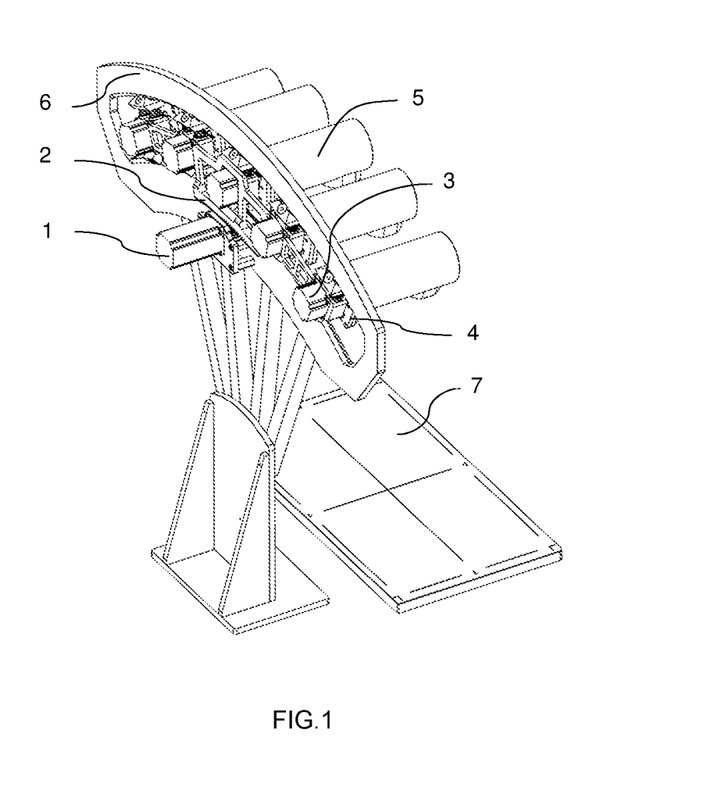
FIG. 1 illustrates an ultrafast 3D digital radiography system with multiple X-ray sources in motion.

A novel ultrafast 3D digital imaging system with multi pulsed X-ray sources is shown in FIG. 1. It comprises a primary motor 1 engaged with a primary motion stage 2, multiple X-ray sources 5, and an X-ray flat panel detector 7. All motors, all motor stages, and X-ray sources are mounted in a supporting frame structure 6.

Each secondary motor 3 is engaged to a secondary motion stage 4. All secondary motion stages 4 are mounted on a primary motion stage 2. Every X-ray source 5 is mounted on a secondary motor stage 4. Every motor is controlled by programmable motion control hardware and can move the motor stage back-and-forth at a predetermined speed. The secondary motor stages 4 are positioned in such a way that spacing to adjacent stages is equal. As a result, all X-ray sources 5 move together with the primary motor stage 2, but each individual X-ray source 5 can also move individually with the secondary motor stage 4.

The X-ray flat panel detector 7 can also be mounted on an additional linear stage. The X-ray flat panel detector 7 can move back-and-forth, based on the location of X-ray sources 5 in order to have a broader coverage of images.

Figure 2:
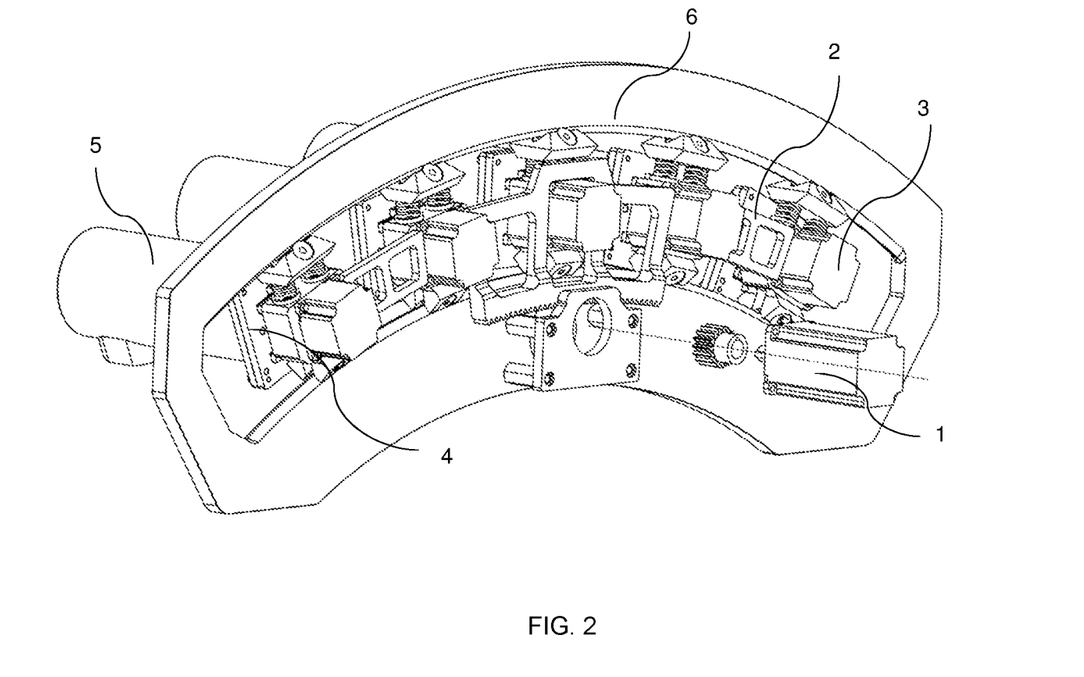
FIG. 2 is a mechanical drawing illustrating that X-ray sources are positioned with motion control.

FIG. 2 shows another exemplary embodiment where secondary motors 3 are interconnected as an assembly of rigid body structure that itself is served as a primary stage 2 because it has rolling wheels at edges. Primary motor 1 engages primary stage 2 by gears. Primary motor 1 can move primary stage 2 along the rigid rail at a predetermined constant speed. Because all secondary motion stages 3 are mounted on they can also move along the rigid rail at a predetermined constant speed. Secondary motor 3 are equally spaced to their neighbor secondary motors 3. Each secondary motor stage 4 can move back-and-forth by a secondary motor 3. An X-ray source 5 is mounted on a secondary motor stage 4. Motion of each X-ray source 5 on a secondary motor stage 4 has four sessions of motion: acceleration; constant speed, deceleration and move back to initial position. At any moment, only one X-ray source 5 can be on a constant speed that move opposite direction to primary motor stage 2. The constant speed of a secondary motor stage 4 is programmed to be equal to the constant speed of the primary motor stage motion 2.

Figure 3:
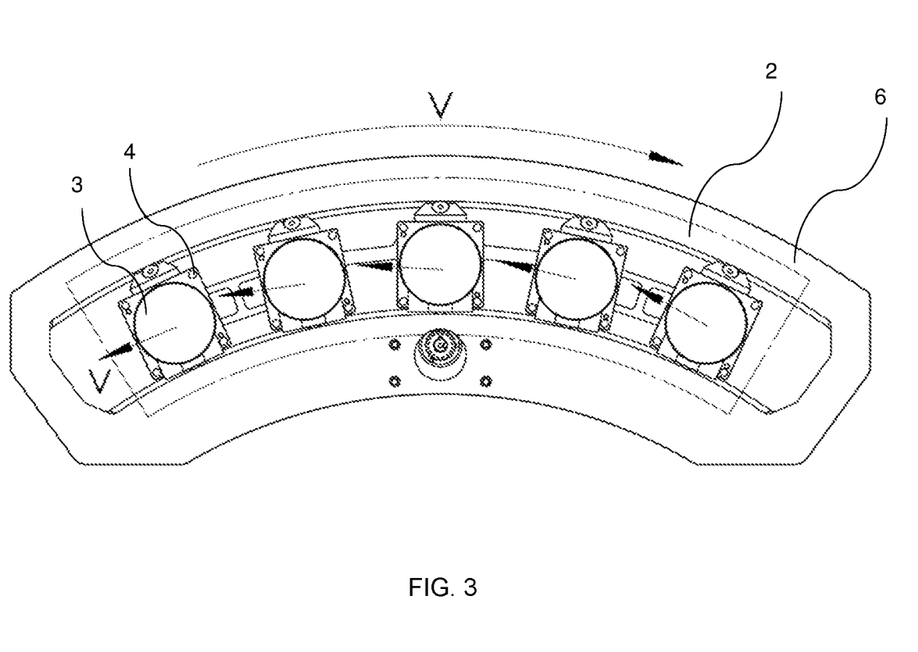
FIG. 3 illustrates that an individual X-ray source emits an X-ray beam in a temporary standstill position at the moment when the primary and secondary motor stages are moving in the opposite direction but with the same speed.

FIG. 3 shows how motion control operation is performed. For one data acquisition cycle, Primary motor stage 2 moves in one direction at a constant speed, then go back to the initial position. While primary motor stage 2 is moving at a constant speed, each of secondary motor stage 4 is vibrating at the predetermined speed. When secondary motor stage 4 travels in the opposite direction to the primary motion stage 1 and has the same constant speed, X-ray source 5 and X-ray flat panel detector 7 are triggered. At this moment of a trigger, an X-ray source 5 behaves just like that the X-ray source 5 is standstill while emitting an X-ray beam. Therefore, the dynamic arrangement of stationary state an X-ray source 5 allows an X-ray imaging system acquires a large number of images from different spatial angle locations in a very short amount of time. Duration of constant speed motion of a secondary motor stage 4 can be programmed by software to match X-ray exposure time. When one secondary motor stage 4 is at the constant speed, the other secondary motor stage 4 could be in acceleration, deceleration, or move back to the initial position in order to get ready for their next constant speed. X-ray sources 5 can also be programmed to perform exposure on-demand based on each independent external trigger pulse in a random sequence.

In view of the widely available superfast computer available, image analysis can be done in real-time with the image acquisition. Judgment on the images taken will have an impact on the X-ray source 5 position for the next shot. There is no need to wait until finish of whole image acquisition to do image reconstruction.

Figure 4:
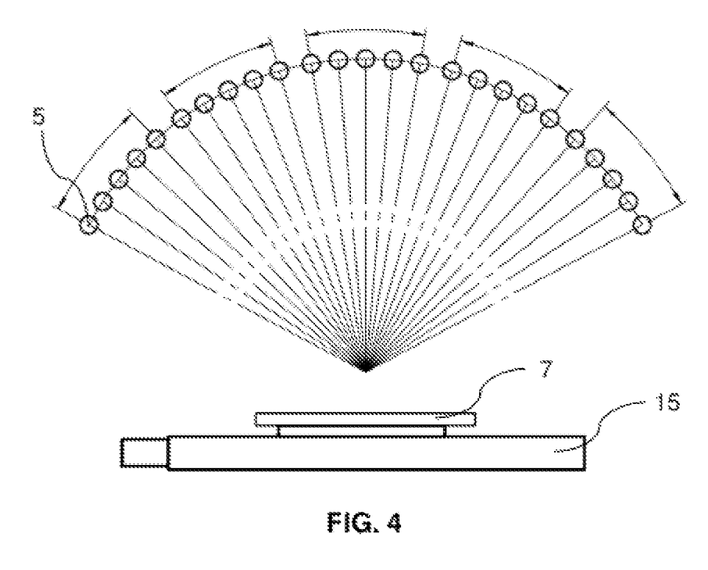
FIG. 4 illustrates that a five-X-ray-source system takes 25 sets of projection data by each traveling only one-fifth of the total distance.

FIG. 4 illustrates a complete exposure position. In this case, there are there are five X-ray sources 5 and the five X-ray sources 5 perform 25 total X-ray exposures at different angle position. But each secondary motor stage 4 only needs to travel one-fifth of total covered angle. Therefore, with multiple X-ray sources 5 working in parallel, a large amount of projection data can be acquired at a fraction of amount of time. X-ray flat panel detector 7 is served as an X-ray receiver.

Electronic signal always go faster than that of mechanical motion, bottle neck of limiting factor is always motor stage motion itself. Next bottleneck is detector readout limitation. Because detector also needs some time to read out many Mega pixel data and then transfer to a computer.

Figure 5:
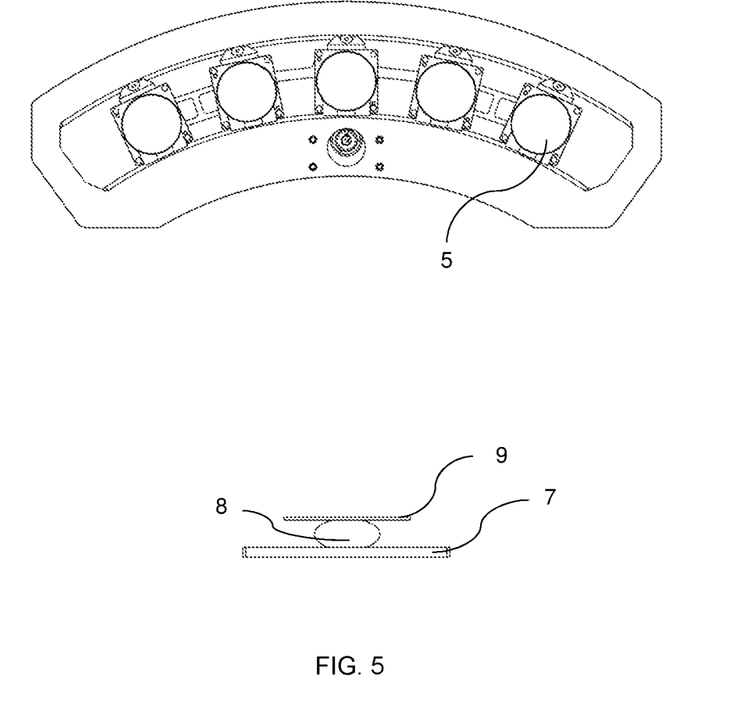
FIG. 5 illustrates that the multi-X-ray-source ultrafast 3D digital radiography system is at full-field mammography with ultrafast tomosynthesis.

FIG. 5 illustrates that the multi-X-ray-source ultrafast 3D digital radiography system is at full-field mammography with ultrafast tomosynthesis. Breast 8 from a woman patient is compressed to X-ray flat panel detector 7 by a compressor 9 in order to get better X-ray projection data. Compared with other mammography systems, the current system can acquire much more data projection and run much faster with reduced pain to women patients.

Figure 6:
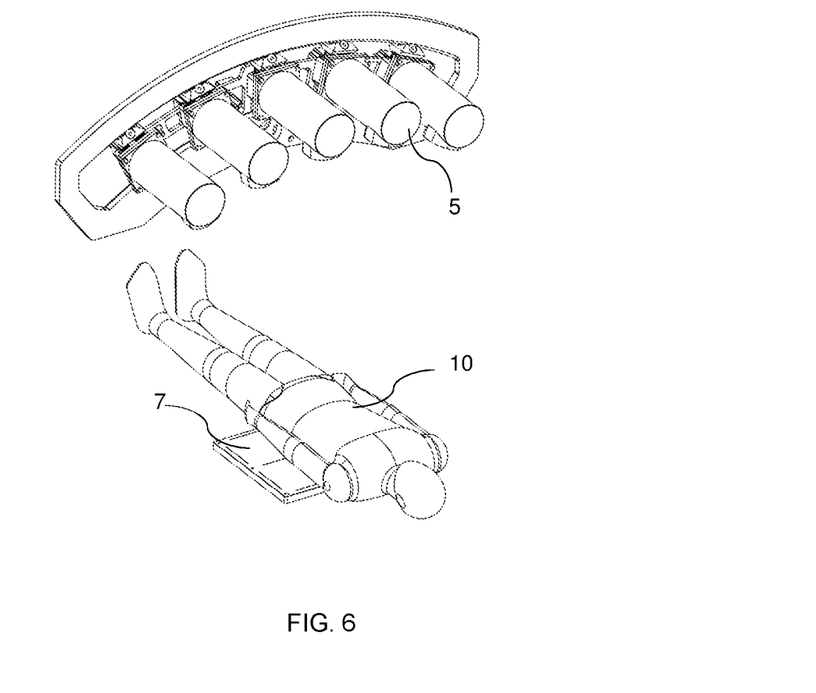
FIG. 6 illustrates that the multi-X-ray-source ultrafast 3D digital radiography system can be used at related 3D chest ultrafast radiography.

FIG. 6 illustrates another embodiment where the multi-X-ray-source ultrafast 3D digital radiography system is used in a COVID-related application mode. An human object 10 is laid down on top of the X-ray flat panel detector 7 to get fast 3D X-ray images for a region of interest. The system can rapidly perform ultrafast 3D chest radiography to check a lung condition because the COVID virus usually damages the human lung. Ultrafast 3D X-ray imaging of a human lung can help with not only monitoring lung condition and but also accurate diagnosing.

Figure 7:
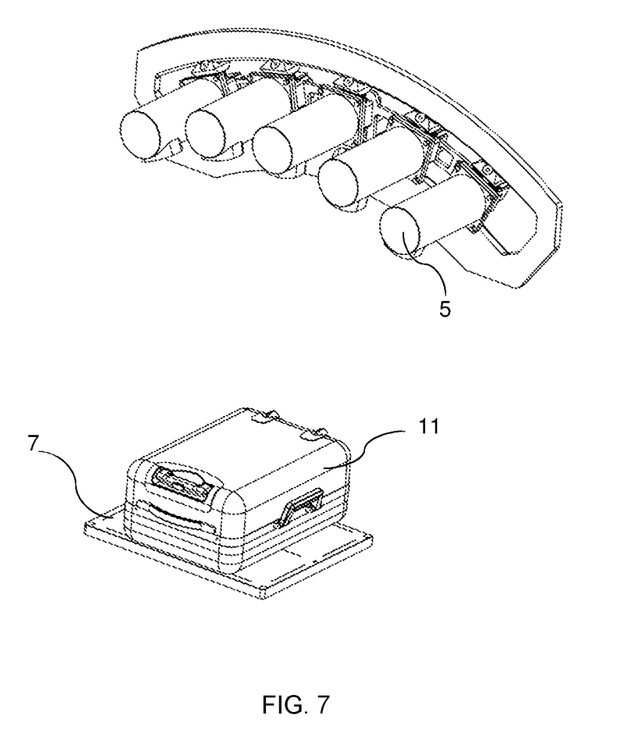
FIG. 7 illustrates that the multi-X-ray-source ultrafast 3D digital radiography system at 3D ultrafast radiography with general NDT or Security application.

FIG. 7 illustrates that the multi-X-ray-source digital radiography system is in general NDT or security inspection application mode. A general object 11 is put on top of X-ray flat panel detector 7 to get fast 3D X-ray images for a region of interest. The system can perform 3D ultrafast radiography with the general object 11. The system thus can provide a fast 3D view of contents inside a luggage case or other objects for security purposes.

The control parameters of X-ray sources 5 such as current (mA), voltage (kV), and exposure duration can be electronically controlled through software. Therefore, the application or user can choose proper mA and kV of X-ray source 5 for various objects.

The primary motor stage 2 can sweep multiple times and each time with a different kV. In this case, the system can acquire dual-energy or multi-energy images for the same object.

X-ray smart scan can also be performed. In this case, X-ray mA, kV, speed and sweep angle etc. will be determined by artificial intelligence (AI). For example, X-ray kV is automatically determined based on the density of an object.

In some cases, operator want to perform X-ray scan at a special region of interest. This can scan range can be narrowed down to very specific scan angle. X-ray multi-angle real-time scans can also performed due to the fact that X-ray sources 5 are from different angles and X-ray flat panel detector 7 is dynamic detector that can read out data at very high speed.

In one embodiment with smart-scan capability, the X-ray sources 5 are activated in a predetermined sequence and use predetermined current/voltage settings for various objects. As the X-ray exposure is from multiple X-ray sources 5 and is from multiple different angles, the system can also perform 4D imaging with time component built-into-image, in addition to standard 3D X-Y-Z spatial information.

Figure 8:
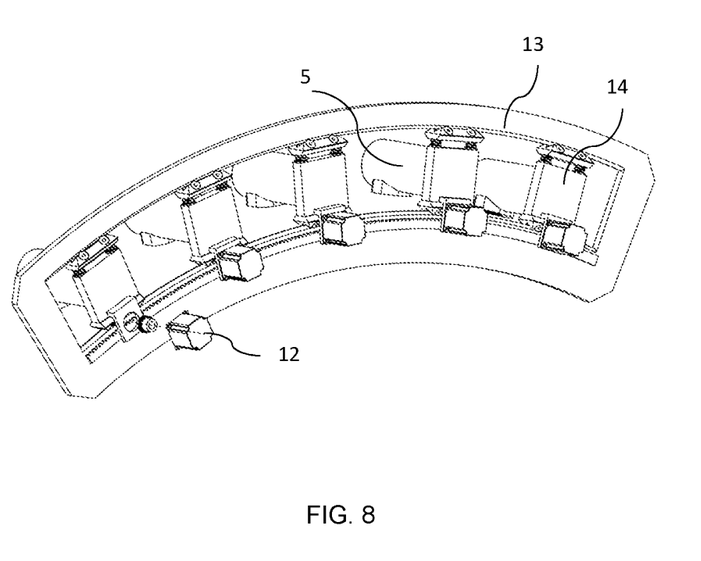
FIG. 8 illustrates another embodiment where the primary motor and primary motor stage can be omitted, and an individual X-ray source can move along a predetermined track with motion control.

FIG. 8 shows another alternative simplified embodiment. An X-ray source 5 is sitting on a direct-contact motor stage 14. The direct-contact motor stage 14 engages with a direct-contact motor 12. Therefore, the direct-contact motor 12 can drive X-ray source 5 to move along a predetermined rail with a long gear. A direct-contact supporting frame structure 13 is used to housing direct-contact motor stage 14 and direct-contact motor 12. In this case, each of the direct-contact motor stage 14 has one of the following states: standstill, acceleration, constant speed, and deceleration. An X-ray source 5 only emits X-ray at a state of standstill. At any moment, only one X-ray source 5 can emit X-ray. A computer with software can easily program the set up where one X-ray source 5 is emitting X-ray while other X-ray sources 5 are in a state of acceleration, constant speed, and deceleration. In this way, the system can also sweep a large angle and also rapidly acquire a large amount of data.

Figure 9:
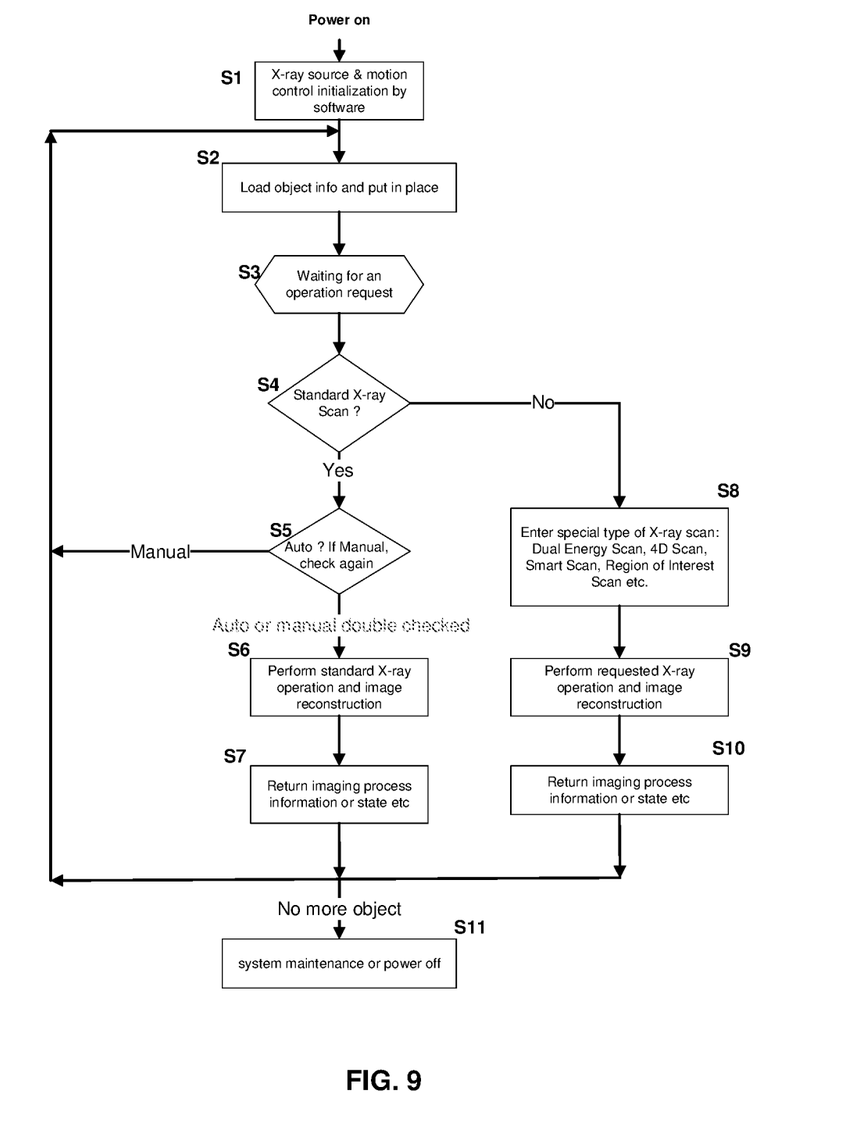
FIG. 9 shows flowchart of an ultrafast 3D digital radiography system operation.

FIG. 9 shows typical flowchart of an ultrafast 3D digital radiography system operation. The ultrafast 3D digital radiography system has several advanced features although most of users just want a standard ultrafast 3D X-ray scan.

Upon power on, the system would need initialization. Software program would need to perform system initialization. X-ray sources 5 usually need to warm up to a state so that X-ray tube and high voltage control electronics are stable. Motion control system would make sure that primary motor stage 2 and multiple secondary motor stages 4 are both at correct initial spatial position. Because each of X-ray sources 5 is mounted at a secondary motor stage 4 and each of secondary motor stages 4 are mounted at primary motor stage 2, then correct positions of primary motor stage 2 and multiple secondary motor stages 4 means correct position of X-ray sources 5. This process is indicated by block of step S1. After initialization, positions of X-ray sources 5 initially are uniformly distributed in a geometry of wide angle and each individual X-ray source 5 only take care of small fraction of scan angle as described in FIG. 4. System is then ready to use with multiple X-ray sources 5 working in parallel.

Block of step S2 is next step. This step is regarding X-ray scan sample preparation. Therefore, step S2 may take a long time depending the nature of an X-ray scan object. If the object is breast of a woman patient there will be breast compression involved plus left and right. If the object is a human whole body or partial body, then the person to be scanned would need to be laid down to correct position. If the object is a live veterinary animal there will be more work to do because it is very common that live animal has problems to listen to instruction from a system operator. However, if a scan object is from an industrial part for NDT or from a luggage for security inspection, then the step S2 can be performed relatively fast.

After both machine and scan object are ready, system operator would need to decide what to do. Block of step S3 is regarding a waiting state that is waiting for operation request. System has many advanced features, but most clients only need ultrafast high-efficient good X-ray radiological images with minimum amount of effort unless something unusual pops up.

At block of step S4, a decision will be made. There are two categories of operation. One is standard operation, the other is non-standard operation with many advanced features added. Standard operation is designed for much large volume, while non-standard operation is designed for much comprehensive study.

If system operator decides to go with standard operation, then there will be another chance at block of step S5 to make X-ray scan slightly more comprehensive at expense of slightly slower operation speed. That is a manual mode at standard operation. It requires that system operator to go back step S2 to double check status of X-ray scan object settings to make sure position is correct, region of interest is correct.

After double check the status of an X-ray scan object, system operator can go to step S6 directly just like a standard automatic X-ray scan. Block of step S6 shows that system performs standard X-ray operation and also perform image reconstruction. Using the novel method of multiple X-ray sources 5 working in parallel, step S6 can perform much faster than other methods in prior art that uses a single X-ray source. Number of X-ray exposures are controlled by software. In current mechanical structure, limit factor of maximum speed from motor speed and read-out speed of X-ray flat panel detector 7.

Once image reconstruction is performed, result will be presented to system operator at step S7. In this step S7, much more detailed information can be obtained within much shorter amount of time compared to prior art. Block of step S7 also allows system operator to repeat whole X-ray scan process multiple times if result is not satisfactory.

If X-ray scan operation requested at block of step S4 is non-standard X-ray operation, then system operator can enter block of step S8. At step S8, system would need system operator to decide what kind of specific X-ray is desired. There are several choices such as dual energy or multi energy can, 4D X-ray scan, Smart X-ray scan and special region of interest scan. Because X-ray scan speed with single X-ray source is much slower in prior art, performing dual energy or multi energy scan, 4D X-ray scan, smart X-ray scan and special region of interest scan is usually not feasible in commercial scale. There are extensive X-ray scans involved so that those kinds of processes would take even longer time in order to obtain desired result. Therefore, in prior art, clients may not be willing to wait for long time to perform such X-ray scans. However, with this novel ultrafast X-ray scan system, all those highly specialized scans are now becoming commercially feasible.

At step S9, system performs requested specific X-ray operation. Not only X-ray operation, but imaging reconstruction is also specific. Therefore, result from imaging processing at step S10 would have a lot more information than that of standard ultrafast X-ray scan. This information usually is presented at computer monitor with very fine screen resolution. If result is not satisfactory, system operator can always perform the operation multiple times until desired result is obtained.

System routinely needs maintenance of one kind or another when there are not many tasks to perform at the machine. Block of step S11 shows that system have opportunities to perform required or recommended maintenance for future operations cycle.

A computer program product may include one or more storage medium, for example; solid state disk, magnetic storage media such as magnetic disk or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

Software that controls the process described above can be stored in a tangible computer-readable storage medium to be used as a computer program product and/or can be transmitted via a computer network or other transmission medium.

The above specific embodiments are illustrative, and many variations can be introduced on these embodiments without departing from the spirit of the disclosure or from the scope of the appended claims. For example, elements and/or features of different examples and illustrative embodiments may be combined with each other and/or substituted for each other within the scope of this disclosure and appended claims.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:
1. A system to provide fast 3D radiography, comprising:
a primary motor stage moving freely along a direction of an arc rail with a predetermined shape at a predetermined speed;
a primary motor that engages with said primary motor stage and controls a speed of the primary motor stage;
a plurality of secondary motor stages coupled to said primary motor stage and move along a direction of the arc rail;
a plurality of secondary motors, each engaging one of the plurality of secondary motor stages and controlling a speed of the plurality of the secondary motor stages, wherein the plurality of secondary motor stages move in an opposite direction to the primary motor stage at said primary motor stage speed;

a plurality of X-ray sources coupled to and moved by one of the plurality of secondary motor stages;

a supporting frame structure that provides housing for the primary motor stage and the plurality of secondary motor stages; and a flat panel detector to receive X-ray imaging data, wherein the plurality of X-ray sources and flat panel detector are triggered when one of the plurality of the secondary motor stages travels in the opposite direction to the primary motor stage at said primary motor stage speed.

2. The system of claim 1, comprising a programmable motion control hardware coupled to the primary and secondary motors that control the speed of the primary and secondary motor stages, wherein the programmable motion control hardware is adjustable by software.

3. The system of claim 1, comprising a programmable motion control hardware coupled to the primary and secondary motors, wherein an initial spatial position of the primary and secondary motor stages is adjustable by software of the programmable motion control hardware.

4. The system of claim 1, wherein a current and a voltage provided to each X-ray source are adjustable.

5. The system of claim 1, wherein an exposure time of each X-ray source is adjustable.

6. The system of claim 1, wherein an object between the plurality of X-ray sources and the flat panel detector is at a standstill.

7. A method of fast 3D radiography comprising:

positioning a primary motor stage and one or more secondary motor stages to a predetermined initial location on an arc rail;

attaching a plurality of X-ray sources to a secondary motor stage;

sweeping the primary motor stage at a sweep angle in a direction along the arc rail and a predetermined constant speed by a primary motor;

oscillating the one or more secondary motor stages in a direction opposite from the direction of the primary motor stage along the arc rail by a corresponding secondary motor with a predetermined sequence;

electrically activating the plurality of X-ray sources and a flat panel detector when one of the one or more secondary motor stages moves in the opposite direction to that of the primary motor stage and at a selected speed of the primary motor stage; and acquiring image data from the plurality of X-ray sources with a flat panel detector.

8. The method of claim 7, comprising calibrating the plurality of X-ray sources located at the predetermined initial location relative to the flat panel detector.

9. The method of claim 7, comprising acquiring dual-energy or multi-energy imaging data by sweeping the primary motor stage two or more times with different X-ray source voltages.

10. The method of claim 7, wherein a smart scan is performed by activating the plurality of X-ray sources in a predetermined sequence.

11. The method of claim 7, further comprising reconstructing the image data, wherein X-ray imaging data is acquired and reconstructed in real-time.

12. The method of claim 7, wherein acquiring image data comprises acquiring 3D imaging data and adding a time component to the 3D imaging data.

13. The method of claim 7, comprising changing the sweep angle based on a region of interest.

14. The method of claim 7, wherein each of the plurality of X-ray sources has a voltage input, comprising changing the X-ray source voltage input based on object density during the sweeping of the primary motor.

15. The method of claim 7, wherein the flat panel detector is coupled to a linear stage to adjust a position based on a location of at least one of the plurality of X-ray sources.

* * * * *